(12) United States Patent
Artsyukhovich et al.

(10) Patent No.: US 9,681,793 B2
(45) Date of Patent: Jun. 20, 2017

(54) SURGICAL PROBE WITH INTERLOCKING ATTACHMENT

(71) Applicant: Novartis AG, Basel (CH)

(72) Inventors: Alex Artsyukhovich, Lake Forest, CA (US); Dustin Bouch, Lake Forest, CA (US); Ron T. Smith, Lake Forest, CA (US)

(73) Assignee: Novartis AG, Basel (CH)

( * ) Notice: Subject to any disclaimer, the term of this patent is extended or adjusted under 35 U.S.C. 154(b) by 429 days.

(21) Appl. No.: 14/309,701

(22) Filed: Jun. 19, 2014

(65) Prior Publication Data

US 2015/0366432 A1  Dec. 24, 2015

(51) Int. Cl.
| | |
|---|---|
| *A61B 1/06* | (2006.01) |
| *A61B 1/00* | (2006.01) |
| *A61B 1/07* | (2006.01) |
| *B23K 26/32* | (2014.01) |
| *B23K 26/211* | (2014.01) |
| *B23K 26/282* | (2014.01) |
| *B23K 101/04* | (2006.01) |
| *B23K 101/20* | (2006.01) |
| *B23K 103/08* | (2006.01) |
| *B23K 103/12* | (2006.01) |
| *B23K 103/18* | (2006.01) |

(52) U.S. Cl.
CPC ............ *A61B 1/0011* (2013.01); *A61B 1/07* (2013.01); *B23K 26/211* (2015.10); *B23K 26/282* (2015.10); *B23K 26/32* (2013.01); *B23K 2201/045* (2013.01); *B23K 2201/20* (2013.01); *B23K 2203/08* (2013.01); *B23K 2203/12* (2013.01); *B23K 2203/18* (2013.01); *Y10T 156/1005* (2015.01)

(58) Field of Classification Search
CPC ................................ A61B 1/0011; A61B 1/07
See application file for complete search history.

(56) References Cited

U.S. PATENT DOCUMENTS

| | | | |
|---|---|---|---|
| 4,859,827 | A | 8/1989 | Coyle, Jr. et al. |
| 5,738,676 | A | 4/1998 | Hammer et al. |
| 5,782,825 | A | 7/1998 | Anderson |
| 5,960,027 | A | 9/1999 | Kiyohara et al. |
| 6,522,827 | B1 | 2/2003 | Loeb et al. |
| 8,764,261 | B2 | 7/2014 | Smith |
| 2003/0219202 | A1 | 11/2003 | Loeb et al. |
| 2007/0027443 | A1 | 2/2007 | Rose et al. |
| 2009/0093800 | A1 | 4/2009 | Auld et al. |
| 2013/0041356 | A1 | 2/2013 | Smith et al. |

FOREIGN PATENT DOCUMENTS

WO  03/051184 A1  6/2003

*Primary Examiner* — Andrew Coughlin

(57) ABSTRACT

A method of manufacturing an optical probe for use in ophthalmic procedures can comprise: positioning a ferrule within a proximal portion of a cannula, wherein an optical fiber extends at least partially through the ferrule towards an optical element disposed within a distal portion of the cannula; and coupling the cannula to the ferrule by applying laser energy to the cannula. An optical probe can be provided that includes a cannula including a proximal portion and a distal portion; a ferrule disposed within the proximal portion of the cannula, the cannula and the ferrule coupled together by engaged deformations in the cannula and the ferrule; and an optical fiber positioned at least partially within the optical probe, the optical fiber configured to receive a light from a light source and guide the light to an optical element positioned within the distal portion of the cannula.

25 Claims, 10 Drawing Sheets

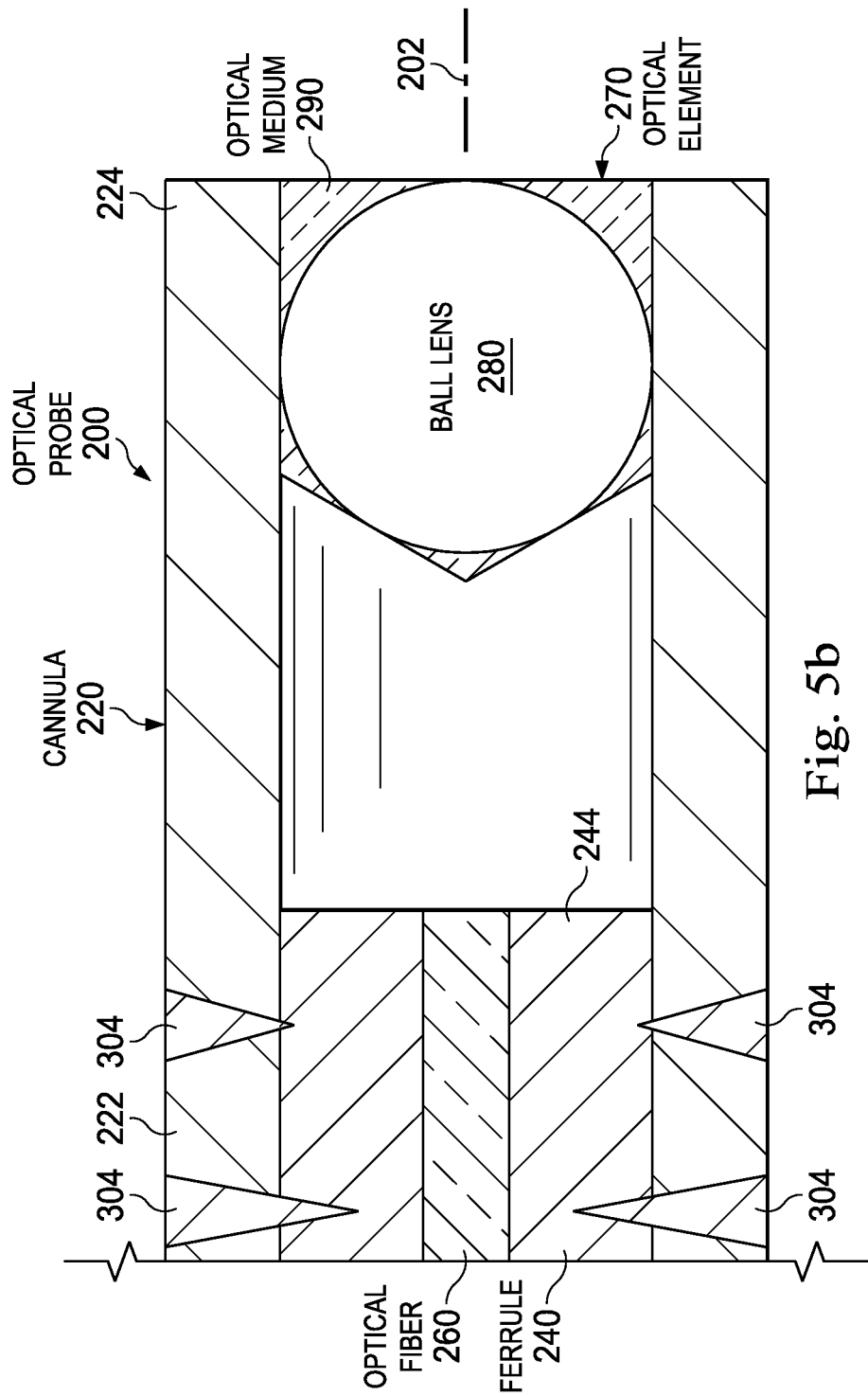

SURGICAL PROBE WITH INTERLOCKING ATTACHMENT

BACKGROUND

Technical Field

Embodiments disclosed herein are related to ophthalmic surgical probes. More specifically, embodiments described herein relate to surgical probe with an interlocking attachment.

Related Art

Ophthalmic surgical probes deliver light to a surgical field for a variety of applications. For example, in pan-retinal photocoagulation of retinal tissue, it can be desirable to deliver laser light to multiple spots on the retina during the procedure. The multiple spots can be generated from a single input beam by splitting the single beam using a diffractive beam splitter. The beam splitter can be fixed at the distal end of a surgical probe using an adhesive. One or more other components of the surgical probe can also be joined using an adhesive. Surgical probes, such as those described in U.S. patent application Ser. No. 12/959,533, filed Dec. 3, 2010, the entirety of which is hereby incorporated by reference, can be used for these applications.

Delivering light to the surgical field can be challenging for several reasons. While most of the light from the split beam can be transmitted to the surgical field, some portion of the light can be absorbed by the surgical probe. Because some components of the surgical probe can be poor heat conductors, "hot spots" in the surgical probe can develop. Degradation and/or failure can result when hot spots develop near components that are joined by an adhesive.

Some improvement in the structural integrity of surgical probes can be achieved using thermally conductive materials such as those described in U.S. patent application Ser. No. 13/565,041, filed Aug. 2, 2012, the entirety of which is hereby incorporated by reference. Using such materials allows for more efficient heat transfer from areas that absorb light and decreases the likelihood that hot spots will develop.

Nevertheless, unusual circumstances can arise during operation of surgical probes that can cause a high temperature failure. For example, blood can become disposed on the distal tip of a surgical probe. Light that would normally pass through surgical probe with high transmittance can be absorbed by the blood. This can cause the blood to heat up to high temperatures. The heat can be conducted towards one or more elements of the surgical probe that are joined by an adhesive, and a temperature in excess of the degradation temperature of the adhesive can result. In some circumstances, one or more elements of the surgical probe can become detached from the probe during a surgical procedure.

Accordingly, there remains a need for improved devices, systems, and methods that improve the structural integrity of surgical probes by addressing one or more of the needs discussed above.

SUMMARY

The presented solution fills an unmet medical need with a unique solution to provide a laser-induced, interlocking attachment to enhance the strength and structural integrity of a cannula/ferrule joint between a proximal assembly and a distal assembly in an optical probe.

Consistent with some embodiments, a method of manufacturing an optical probe for use in ophthalmic procedures comprises: positioning a cannula around a distal portion of a ferrule, wherein an optical fiber extends at least partially through the ferrule towards an optical element disposed within a distal portion of the cannula; and coupling the cannula to the ferrule by applying laser energy to the cannula.

Consistent with some embodiments, an ophthalmic surgical apparatus comprises: an optical probe having a ferrule; a cannula disposed around a distal portion of the ferrule, the cannula and the ferrule coupled together by engaged deformations in the ferrule and the cannula; and an optical fiber positioned at least partially within the optical probe, the optical fiber configured to receive a light from a light source and guide the light to an optical element positioned within a distal portion of the cannula.

Consistent with some embodiments, an ophthalmic surgical system, comprises: a light source configured to generate a light; and an optical probe that is optically connected with the light source, the optical probe including a ferrule; a cannula disposed around a distal portion of the cannula, the cannula and the ferrule coupled together by engaged deformations in the ferrule and the cannula; and an optical fiber positioned at least partially within the optical probe, the optical fiber configured to receive the light from the light source and guide the light to an optical element positioned within a distal portion of the cannula.

Additional aspects, features, and advantages of the present disclosure will become apparent from the following detailed description.

BRIEF DESCRIPTION OF THE DRAWINGS

FIG. 5b is a diagram illustrating an optical probe.

Figure 1:
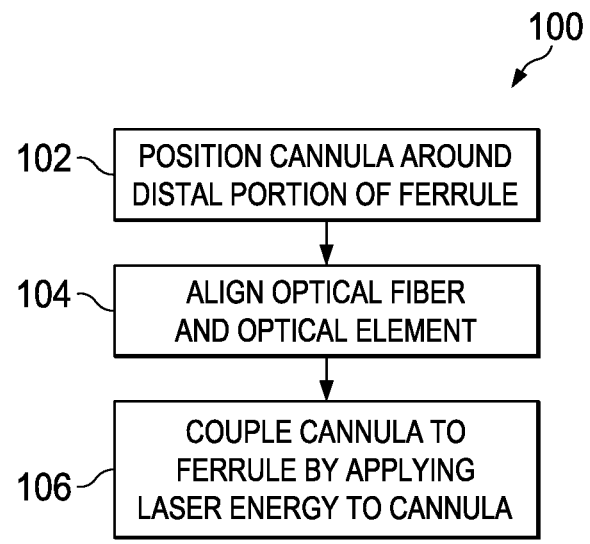
FIG. 1 is a flow diagram illustrating a method of manufacturing an optical probe with an interlocking attachment for use in ophthalmic procedures.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

The present disclosure describes a mechanical interference and/or interlocking configuration based on the application of laser energy to a cannula/ferrule joint in an optical probe. The interlocking attachment in the cannula/ferrule joint provides for a more thermally robust optical probe. That is, optical probes according to the present disclosure can be less susceptible to high temperature failure.

The devices, systems, and methods of the present disclosure provide numerous advantages, including: (1) the ability to withstand higher temperatures with less risk of degradation of the cannula/ferrule joint; (2) the decreased likelihood of the cannula becoming detached from the ferrule during a surgical procedure; (3) providing a secondary means (e.g., in addition to an adhesive) to strengthen and preserve the structural integrity of the cannula/ferrule joint; (4) the ability to continue the use of a thermally conductive bonding material in the cannula/ferrule joint; and (5) the ability to manufacture in a cost-effective manner suitable for a disposable component.

FIG. 1 provides a flow diagram of a method 100 of manufacturing an optical probe with an interlocking attachment for use in ophthalmic procedures. The method 100 can include positioning a cannula around a distal portion of a ferrule (step 102). An optical fiber can extend at least partially through the ferrule towards an optical element that can be disposed within a distal portion of the cannula. The method 100 can include applying a bonding material to the ferrule and/or the cannula. Positioning the cannula in the method 100 can include aligning the optical fiber and the optical element for optical communication (step 104). The method 100 can include coupling the cannula to the ferrule by applying laser energy to the cannula (step 106). Coupling the cannula to the ferrule in method 100 can include applying the laser energy around a perimeter of the cannula. The laser energy can be applied intermittently or continuously around the perimeter of the cannula.

Coupling the cannula to the ferrule in the method 100 can include generating engaged deformations in the cannula and the ferrule. Generating engaged deformations in the method 100 can include generating an interlock feature that restricts longitudinal displacement of the cannula relative to the ferrule. The engaged deformations can include a recess in the ferrule and/or an inward radial protrusion in the cannula. Coupling the cannula to the ferrule in the method 100 can include directly and/or indirectly engaging the protrusion of the cannula to the recess of the ferrule. A bonding material can be disposed between the cannula and the ferrule. The method 100 can additionally include selecting values for at least one or more of the following variable parameters suitable to generate the engaged deformations: wavelength, power, power density, pulse pattern, peak irradiance, pulse duration, and spot size of the laser energy.

The method 100 can be further understood with reference to FIGS. 2a-6 that illustrate cross-sectional views of an optical probe 200 during various stages of the method 100. In that regard, a distal portion of the optical probe 200 can be seen in FIGS. 2a-6. The optical probe 200 can include one or more additional elements proximal of the ferrule 240. For example, the optical probe 200 can include a handpiece, a handle, etc. The optical probe 200 can include a longitudinal axis 202.

The optical probe 200 can include a cannula 220. The cannula 220 can be configured to be inserted through the sclera, into an eye during an ophthalmic surgical procedure. The cannula 220 can be positioned coaxial with or parallel to the longitudinal axis 202. The cannula 220 can be formed of or include a material with a high thermal conductivity. A high thermal conductivity material can facilitate the transfer of heat across the cannula 220 and between different elements of the optical probe 200. A high thermal conductivity material can also prevent localized hot spots. The cannula 220 can also be formed of or include a material having a high melting point. A high melting point material can prevent unintended degradation of the cannula 220 at temperatures that can arise during an ophthalmic surgical procedure. For example, the cannula 220 can be formed of or include a metal such as platinum, palladium, gold, or other suitable material(s).

The cannula 220 can include a proximal portion 222 and a distal portion 224. The cannula 220 can include an optical element 270 positioned within the distal portion 224. The cannula 220 and the optical element 270 can be collectively described as a distal assembly of the optical probe 200. The optical element 270 can be configured to receive and transmit light away from the optical probe 200 and into the surgical field (e.g., onto the retina) during an ophthalmic procedure. The optical element 270 can also be configured to split a beam of light into multiple sub-beams and to focus the sub-beams as they are transmitted into the surgical field. For example, the optical element 270 can include a ball lens 280 and an optical medium 290. The optical medium 290 can be formed of or include glass or an optical adhesive. The optical medium 290 can include facets on the proximal or light-receiving surface that can split a beam of light into multiple sub-beams. The multiple sub-beams can be focused by the ball lens 280. The ball lens 280 can be formed of or include sapphire, cubic zirconium, BK7 glass, or other suitable material(s).

The optical probe 200 can include a ferrule 240. The ferrule 240 can be positioned coaxial with or parallel to the longitudinal axis 202. As similarly described with respect to the cannula 220, the ferrule 240 can also be formed of or include a material with a high thermal conductivity and/or a high melting point. For example, the ferrule 240 can be formed of or include a metal such as platinum, palladium, gold, copper, or other suitable material(s).

An optical fiber 260 can extend through the ferrule 240. The optical fiber 260 can extend through other elements of the optical probe 200 positioned proximal of the ferrule 240, such as a handpiece. The optical fiber 260 can also extend outside of the optical probe 200. The ferrule 240 and the optical fiber 260 can be collectively described as a proximal assembly of the optical probe 200. The optical fiber 260 can be configured to receive light from a light source 310 (as illustrated in, e.g., FIG. 7) and to direct the light towards the optical element 270. The optical fiber 260 can be a single fiber or a fiber bundle.

Figure 2A:
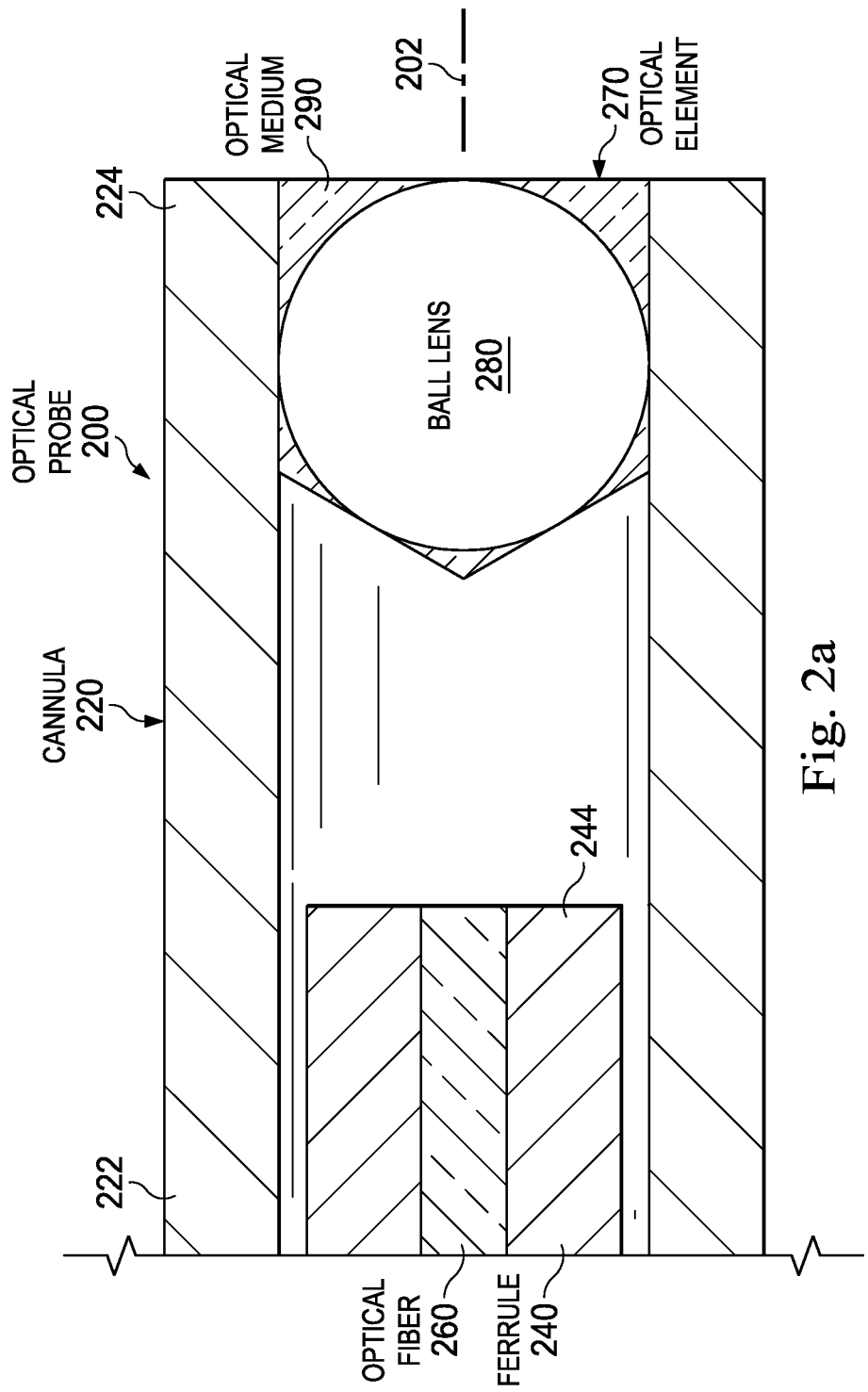
FIG. 2a is a diagram illustrating an optical probe.
Figure 2B:
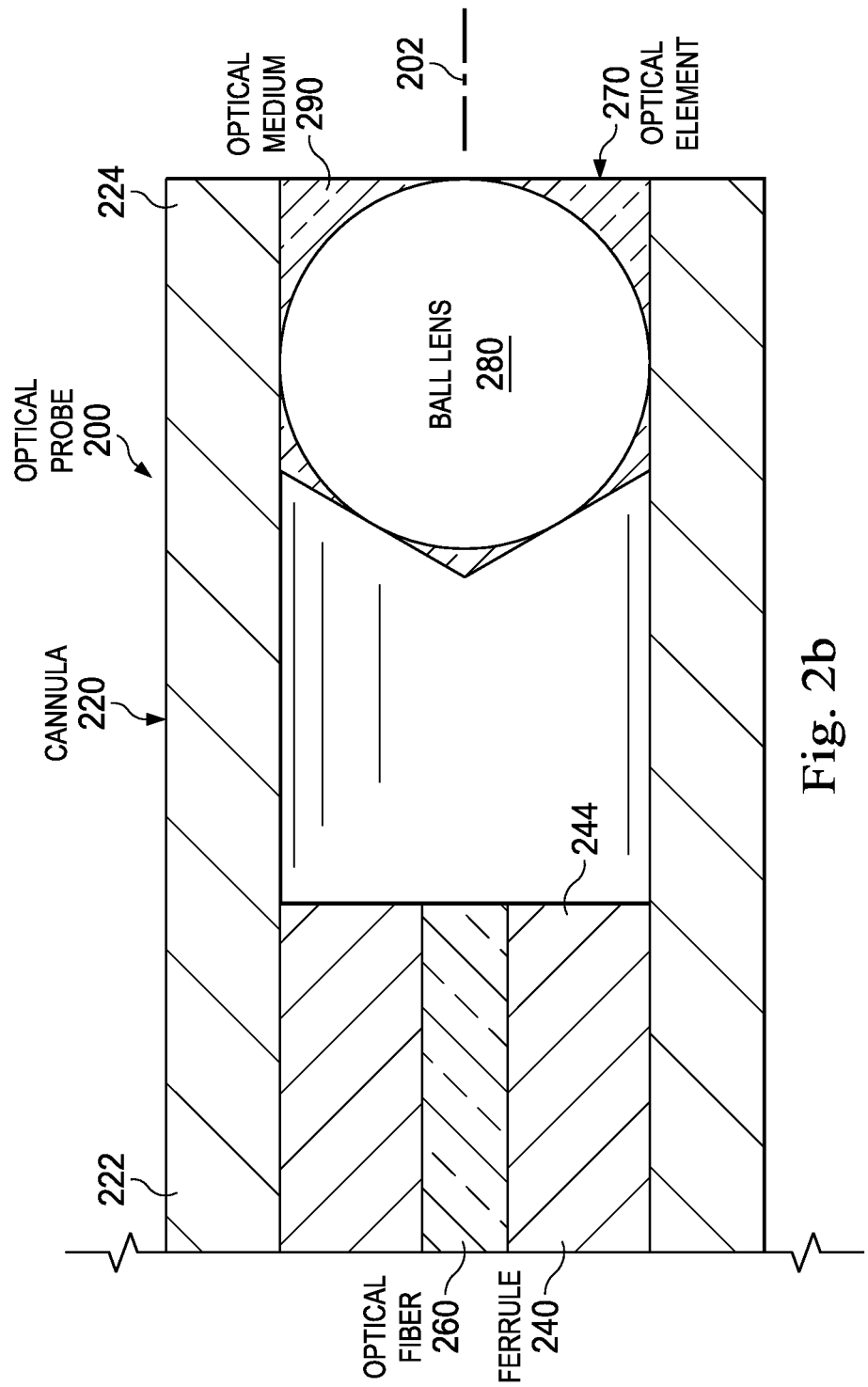
FIG. 2b is a diagram illustrating an optical probe.

Referring to FIGS. 1, 2a, and 2b, at step 102, the method 100 can include positioning the proximal portion 222 of the cannula 220 around a distal portion 244 of the ferrule 240. All or some portion of the ferrule 240 can be positioned and/or disposed within the cannula 220. For example, the distal portion 244 of the ferrule 240 can be positioned within the cannula 220 while a proximal portion can be positioned within an element of the optical probe 200 proximal of the ferrule 240, such as a handle. The cannula 220 can be positioned coaxial with or parallel to the ferrule 240. Positioning the cannula 220 around the ferrule 240 can be described as positioning the distal assembly at least partially around the proximal assembly. The ferrule 240 and/or the cannula 220 can be variously moved relative to one another during method 100 (e.g., the cannula 220 can be positioned around the ferrule 240, the ferrule 240 can be positioned within the cannula 220, etc.).

FIGS. 2a and 2b can be understood to provide similar disclosure of the optical probe 200. However, FIG. 2a illustrates an embodiment in which space can be left between the ferrule 240 and the cannula 220 when the cannula 220 is positioned around the ferrule 240. As described in the discussion of FIG. 3 (and shown in FIGS. 4a, 5a, 6a, and 7a), this space can be filled with a bonding material to couple the ferrule 240 and the cannula 220. The ferrule 240 and cannula 220 can be sized and shaped such that the ferrule 240 and the cannula 220 can be in contact when the cannula 220 is positioned around the ferrule 240. The embodiment shown in FIG. 2b (and in FIGS. 4b, 5b, 6b, and 7b) can substantially omit the space between the ferrule 240 and the cannula 220 such that the ferrule 240 is press fit, slip fit, compression fit, interference fit, or otherwise engagingly fit within the cannula 220. In such embodiments, the bonding material may be omitted.

Referring again to FIGS. 1, 2a, and 2b, at step 104, the method 100 can include aligning the optical fiber 260 with the optical element 270. In that regard, the cannula 220 can be positioned around the ferrule 240 such that the optical fiber 260 and the optical element 270 become aligned. Alignment can include translation and/or rotation of the ferrule 240, the optical fiber 260, and/or the proximal assembly (or vice versa) relative to the cannula 220, the optical element 270, and/or the distal assembly. Translation can occur along and/or parallel to the longitudinal axis 202 and/or in an x-y plane perpendicular to the longitudinal axis 202. The rotation can be about the longitudinal axis 202. Alignment of the optical fiber 260 and the optical element 270 can result in optimum positioning of the focus of the sub-beams of light within the surgical field. For example, the focus of the sub-beams can be configured to be positioned on the retina during use.

Figure 3:
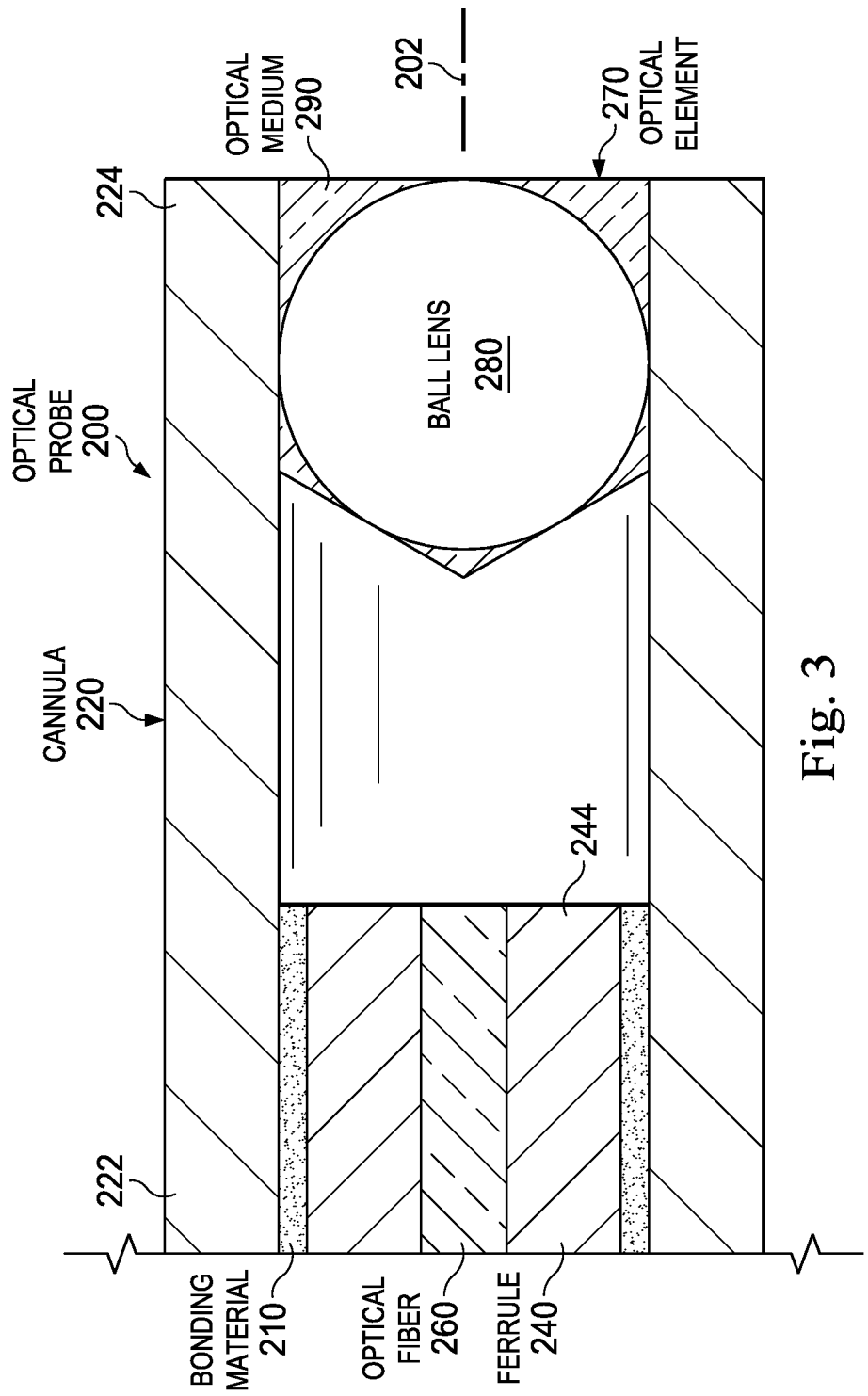
FIG. 3 is a diagram illustrating an optical probe.

Referring to FIG. 3, the method 100 can include applying a bonding material 210 to the cannula 220 and/or the ferrule 240. For example, the bonding material 210 can be applied to an exterior surface of the ferrule 240 before the cannula 220 is positioned around the ferrule 240. After the bonding material is applied, the cannula 220 can be moved to align the optical element 270 and the optical fiber 260, and/or to position the cannula 220 around the ferrule 240. FIG. 3 illustrates that the bonding material 210 can be disposed between proximal portion 222 of the cannula 220 and the ferrule 240. The bonding material 210 can maintain the alignment of the optical fiber 260 with the optical element 270, as obtained in step 104, during subsequent processing of the optical probe 200. The bonding material 210 can be configured to couple the cannula 220 and the ferrule 240. Accordingly, once the bonding material 210 cures, the cannula 220, the optical element 270, and/or the distal assembly can be immobilized relative to the ferrule 240, the optical fiber 260, and/or the proximal assembly to. The bonding material 210 can be formed of or include a high thermal conductivity material. For example, the bonding material 210 can be an adhesive with metal particles included therein, such as silver or other suitable materials. Using a high thermal conductivity bonding material can facilitate efficient heat transfer and reduce the likelihood of hot spots. Adhesives or epoxies such as EpoTek H20E and EpoTek 353ND, available from Epoxy Technologies, Inc. of Billerica, Mass., can be used as the bonding material 210. As described with respect to FIG. 2b, some embodiments can omit step 104.

Figure 4A:
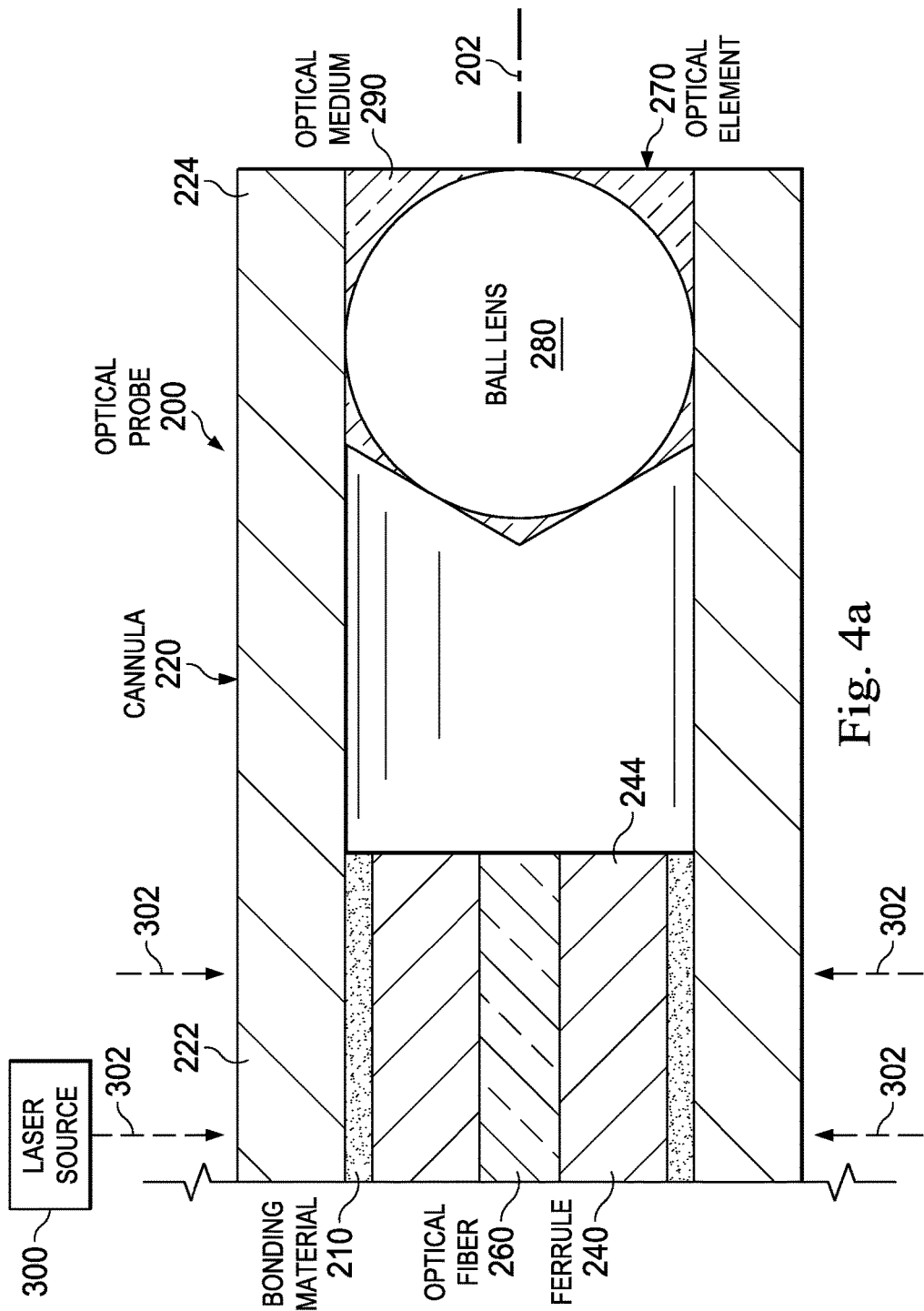
FIG. 4a is a diagram illustrating an optical probe.
Figure 4B:
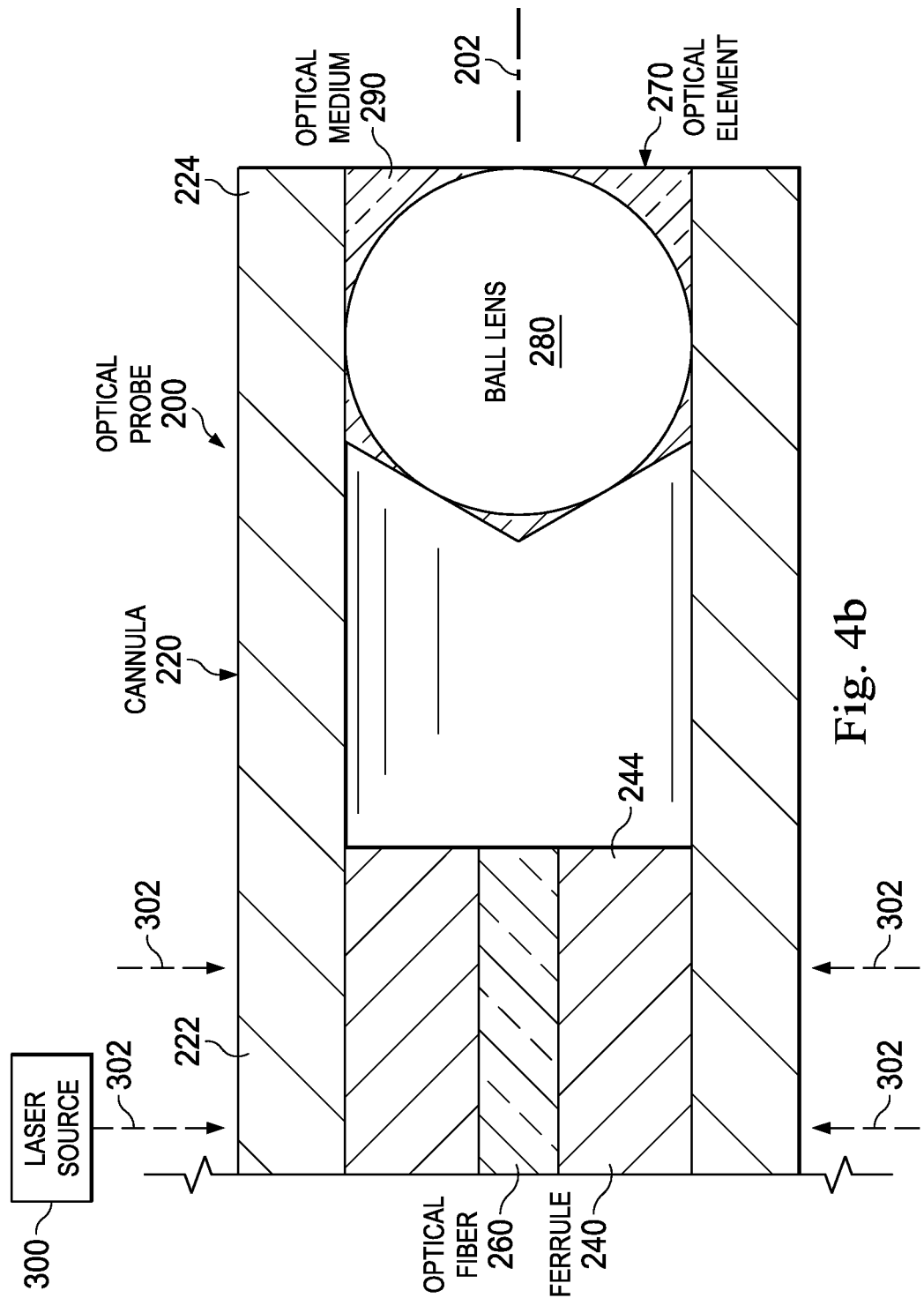
FIG. 4b is a diagram illustrating an optical probe.
Figure 5A:
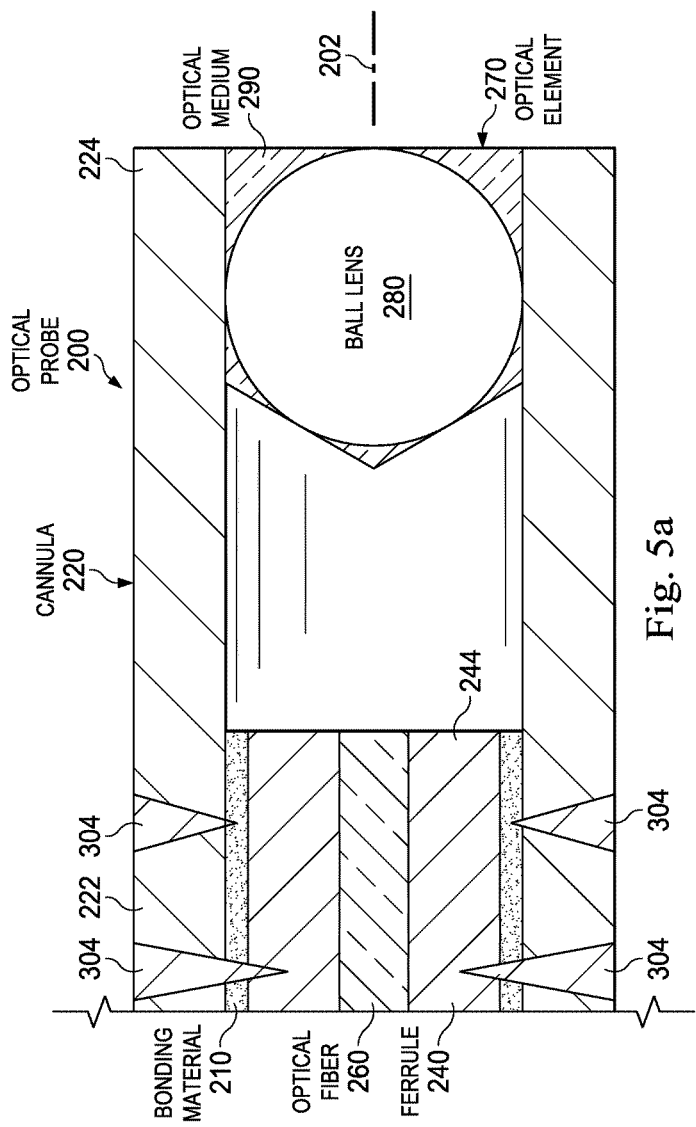
FIG. 5a is a diagram illustrating an optical probe.

Referring to FIGS. 1, 4a, 4b, 5a, and 5b, at step 106, the method 100 can include coupling the cannula 220 to the ferrule 240 by applying laser energy to the cannula 220. As shown in FIGS. 4a and 4b, a laser source 300 can be used to generate laser energy. FIGS. 5a and 5b illustrate areas 304 where the laser energy can be applied in the optical probe 200. Areas 304 can terminate at a point, which can be illustrative of the applications 302 of laser energy using a focused beam. Areas 304 can extend to various depths. Applications 302 of laser energy can penetrate the cannula 220, bonding material, and/or ferrule 240 to various depths.

Applications 302 of laser energy can be carried out around the perimeter of the cannula 220, either continuously or intermittently. For example, the laser energy can be applied to form intermittent mechanical interference around the circumference of the cannula 220 at multiple locations that are a fixed and/or variable distance apart. In other embodiments, the laser energy can be applied to form continuous mechanical interference around the circumference of the cannula 220.

The method 100 can include selecting at least one of a wavelength, a power, a power density, a pulse pattern, a peak irradiance, a pulse duration, and a spot size of the laser energy that can be applied to the cannula 220. In some embodiments, the laser source 300 can be selected from among multiple laser sources to achieve the desired set of laser energy characteristics. In other embodiments, settings of the laser source 300 can be adjusted. For example, peak irradiance can be chosen to be high such that sufficient power can be delivered to the cannula 220 to deform the cannula 220, bonding material 210, and/or ferrule 240 to create engaged deformations. The pulse duration can be chosen such that the laser energy can be applied for a sufficient duration to deform the cannula 220, bonding material 210, and/or ferrule 240 to an intended depth. The spot size can be chosen to be small (e.g., the laser energy can result from a focused beam). Choosing an optimal pulse duration and spot size, among other characteristics, can prevent unintended areas of the optical probe 200 from being affected by the applications 302 of laser energy. For example, the pulse duration can be chosen such that it can be short enough to prevent to the laser energy from diffusing away from the target location that could result in unintended deformation of elements of the optical probe 200.

The application 302 of laser energy to the area 304 can cause the cannula 220 to deform in a localized area. The heat from the application 302 of laser energy, which can cause the cannula 220 to deform, can be conducted through to the ferrule 240. As a result, the ferrule 240 can also deform in a localized area. The materials (e.g., metals) forming the cannula 220 and the ferrule 240 can fuse as both are deformed (e.g., melted). The application 302 of laser energy can be discontinued to allow the cannula 220 and the ferrule 240 to solidify before application of additional laser energy to the same or different portion of the cannula 220 and/or ferrule 240. In this manner engaged deformations in the cannula 220 and the ferrule 240 can be created.

Figure 6A:
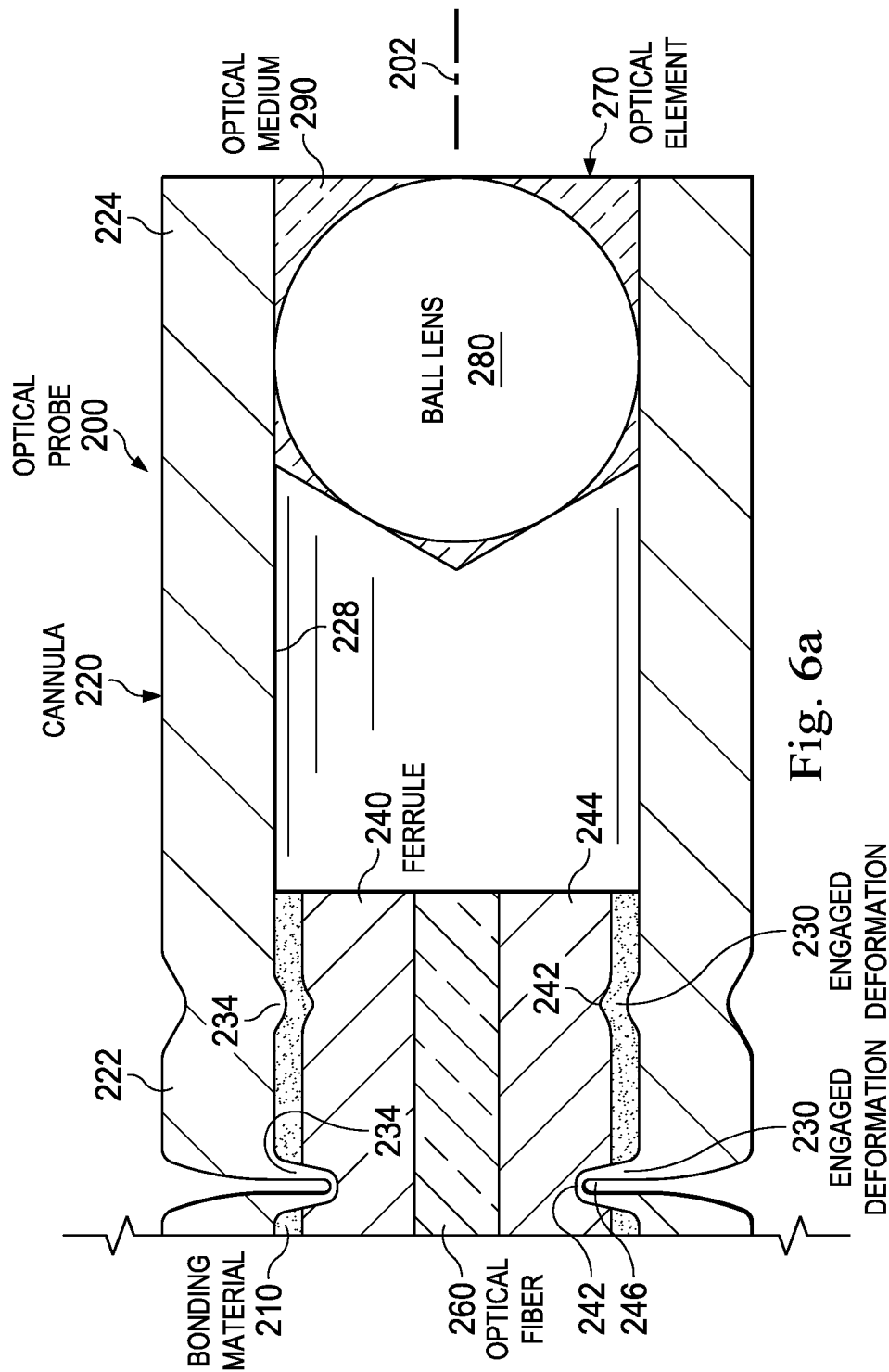
FIG. 6a is a diagram illustrating an optical probe.
Figure 6B:
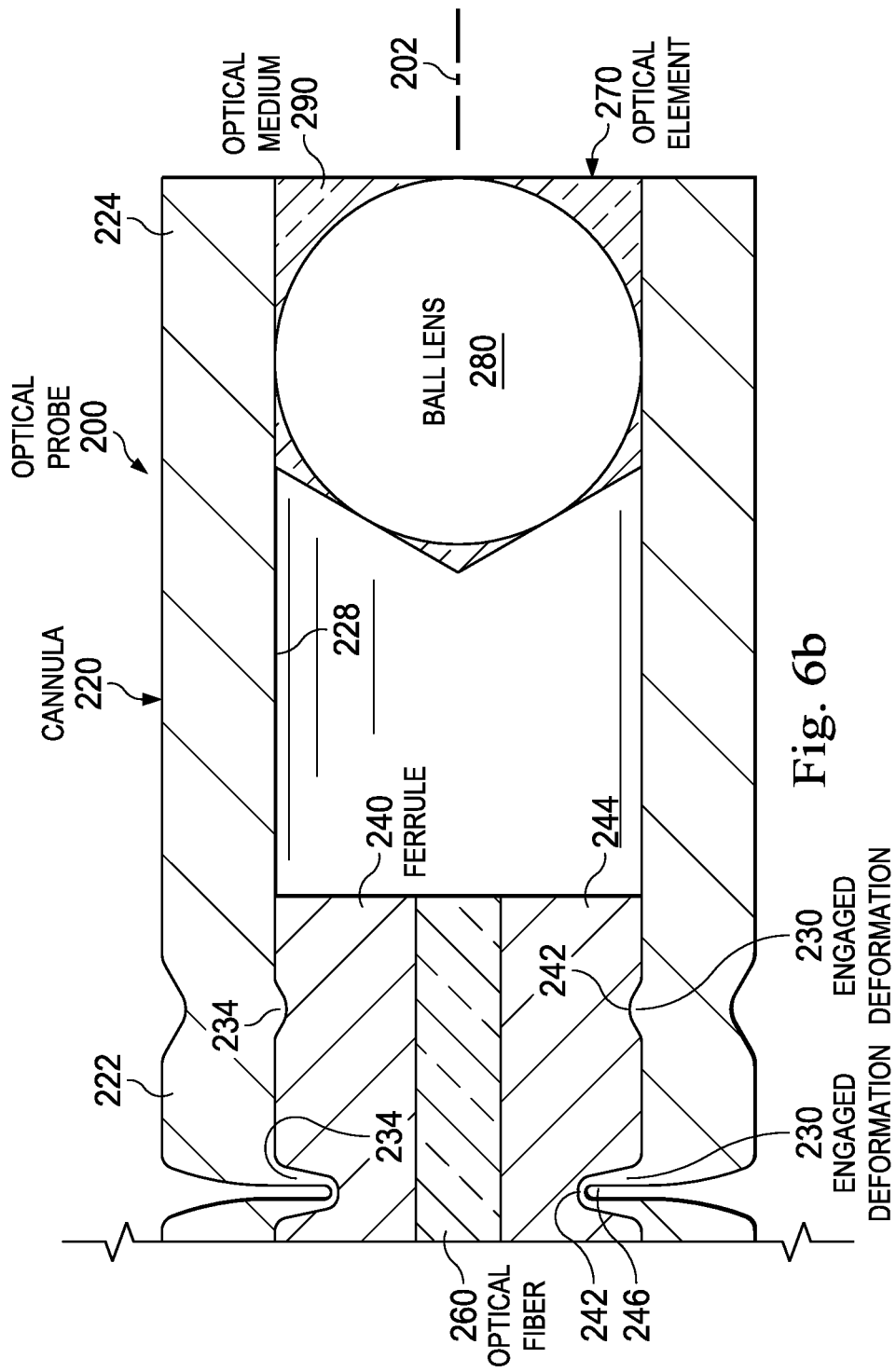
FIG. 6b is a diagram illustrating an optical probe.

FIGS. 6a and 6b each illustrate an assembled optical probe 200 having engaged deformations 230. As shown, the optical probe 200 can have a ferrule 240. The optical probe 200 can have a cannula 220 disposed around a distal portion 244 of the ferrule 240. The cannula 220 and the ferrule 240 can be coupled together by engaged deformations 230 in the cannula 220 and the ferrule 240. The optical probe 200 can have an optical fiber 260 positioned at least partially within the optical probe 200. The optical fiber 260 can be configured to receive a light from a light source and guide the light to an optical element 270 positioned within a distal portion 224 of the cannula 220.

The engaged deformations 230 can be the result of changes in the geometry of the cannula 220, the bonding material 210, and/or the ferrule 240 caused by the application 302 of laser energy. For example, the cannula 220, the bonding material 210, and/or the ferrule 240 can melt, burn, etc., in a desired manner upon the application 302 of laser energy. The engaged deformations 230 can provide direct and/or indirect mechanical engagement between the cannula 220 and the ferrule 240 such that relative motion (e.g., translation and/or rotation) between the cannula 220 and the ferrule 240 can be restricted.

The engaged deformations 230 can include a recess 242 in the ferrule 240. The recess 242 can be an area of inward, radial depression of the ferrule 240 that can arise upon the application of laser energy to the cannula 220 to such a depth that it deforms the ferrule 240. The recess 242 can be directly or indirectly engaged with the cannula 220. The engaged deformations 230 can also include an inward, radial protrusion 234 in the cannula 220. The inward, radial protrusion 234 can extend to various depths into the ferrule 240.

As illustrated in FIG. 6a, the inward, radial protrusion 234 can extend through bonding material 210. As illustrated in FIG. 6b, the inward, radial protrusion 234 can extend directly into the recess 242 of the ferrule 240. In some embodiments, the inward, radial protrusion 234 includes an opening 246 (e.g., as shown on the left engaged deformation 230 of FIGS. 6a and 6b). The opening 246 can extend from the outer surface to the inner surface of the cannula 220 through the inward, radial protrusion 234. In other embodiments, the application 302 of laser energy can be such that the inward, radial protrusion 234 does not include an opening 246 (e.g., as shown on the right engaged deformation 230 of FIGS. 6a and 6b). In that regard, the laser energy can be applied to form inward, radial protrusions 234 with or without an opening as desired.

The engaged deformations 230 can provide an interlock that restricts longitudinal displacement of the cannula 220 relative to the ferrule 240. In general, interlocks include geometrical features of the cannula 220, the bonding material 210, and/or the ferrule 240 that prevent translation and/or rotation of the cannula 220 and/or the ferrule 240 relative to one another. One or more engaged deformations 230 in the cannula 220, the bonding material 210, and/or the ferrule 240 can define the interlock.

Figure 7:
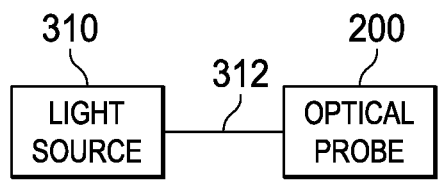
FIG. 7 is a diagram illustrating an ophthalmic surgical system.

FIG. 7 illustrates an ophthalmic surgical system incorporating the optical probe 200. The ophthalmic surgical system can include a light source 310 configured to generate a light. The ophthalmic surgical system can include the optical probe 200 in optical communication with the light source 310. For example, an optical fiber 312 can optically couple the light source 310 and the optical probe 200. The optical probe 200 can include features similar to those described above. For example, the optical probe can include a ferrule 240. The optical probe 200 can also include a cannula 220 disposed around a distal portion 244 of the ferrule 240. The cannula 220 and the ferrule 240 can be coupled together by engaged deformations 230 in the ferrule 240 and the cannula 220. The optical probe 200 can include an optical fiber 260 positioned at least partially within the optical probe 200. The optical fiber 260 can be configured to receive the light from the light source 310 and guide the light to an optical element 270 positioned within a distal portion 224 of the cannula 220.

Embodiments as described herein can provide devices, systems, and methods that facilitate a thermally robust optical probe with interlocking attachment. The devices, systems, and methods described herein can be used with any surgical probe including a distal assembly and a proximal assembly that can be coupled. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. A method of manufacturing an optical probe for use in ophthalmic procedures, comprising:
   positioning a cannula around a distal portion of a ferrule, wherein an optical fiber extends at least partially through the ferrule towards an optical element disposed within a distal portion of the cannula;
   coupling the cannula to the ferrule by applying laser energy to the cannula; and
   generating engaged deformations in the cannula and the ferrule.

2. The method of claim 1, further comprising:
   applying a bonding material to at least one of the cannula and the ferrule.

3. The method of claim 1, wherein positioning the cannula includes:
   aligning the optical fiber and the optical element for optical communication.

4. The method of claim 1, wherein generating engaged deformations includes:
   generating an interlock feature that restricts longitudinal displacement of the cannula relative to the ferrule.

5. The method of claim 1, wherein generating engaged deformations includes:
   generating a recess in the ferrule.

6. The method of claim 5, wherein generating engaged deformations includes:
   generating an inward radial protrusion in the cannula.

7. The method of claim 6, wherein coupling the cannula to the ferrule includes:
   indirectly engaging the protrusion of the cannula to the recess of the ferrule through a bonding material disposed between the cannula and the ferrule.

8. The method of claim 6, wherein coupling the cannula to the ferrule includes:
   directly engaging the protrusion of the cannula to the recess of the ferrule.

9. The method of claim 1, further comprising:
   selecting at least one of a wavelength, a power, a power density, a pulse pattern, a peak irradiance, a pulse duration, and a spot size of the laser energy suitable to generate the engaged deformations.

10. The method of claim 1, wherein coupling the cannula to the ferrule includes:
    applying the laser energy around a perimeter of the cannula.

11. The method of claim 10, wherein:
    the laser energy is applied intermittently around the perimeter of the cannula.

12. The method of claim 10, wherein:
    the laser energy is applied continuously around the perimeter of the cannula.

13. An optical probe comprising:
    a ferrule;
    a cannula disposed around a distal portion of the ferrule, the cannula and the ferrule coupled together by engaged deformations in the cannula and the ferrule; and
    an optical fiber positioned at least partially within the optical probe, the optical fiber configured to receive a light from a light source and guide the light to an optical element positioned within a distal portion of the cannula.

14. The optical probe of claim 13, wherein: the cannula is positioned coaxially relative to the ferrule.

15. The optical probe of claim 13, further comprising:
a bonding material disposed between the ferrule and the cannula, and configured to couple the ferrule and the cannula.

16. The optical probe of claim 13, wherein: the deformations are laser generated deformations.

17. The optical probe of claim 13, wherein: the deformations define an interlock feature restricting longitudinal displacement of the cannula relative to the ferrule.

18. The optical probe of claim 13, wherein: the engaged deformations include a recess in the ferrule.

19. The optical probe of claim 18, wherein: the engaged deformations include an inward radial protrusion in the cannula.

20. The optical probe of claim 19, wherein: the inward radial protrusion of the cannula indirectly engages the recess of the ferrule through a bonding material disposed between the cannula and the ferrule.

21. The optical probe of claim 19, wherein: the inward radial protrusion of the cannula directly engages the recess of the ferrule.

22. The optical probe of claim 19, wherein: an opening extends from an outer surface of the cannula through the inward radial protrusion.

23. The optical probe of claim 13, wherein: the engaged deformations are intermittently disposed around a perimeter of the cannula.

24. The optical probe of claim 13, wherein: the engaged deformations are continuously disposed around a perimeter of the cannula.

25. An ophthalmic surgical system, comprising:
a light source configured to generate a light; and
an optical probe in optical communication with the light source, the optical probe including:
  a ferrule;
  a cannula disposed around a distal portion of the ferrule, the cannula and the ferrule coupled together by engaged deformations in the cannula and the ferrule; and
  an optical fiber positioned at least partially within the optical probe, the optical fiber configured to receive the light from the light source and guide the light to an optical element positioned within a distal portion of the cannula.

* * * * *